United States Patent [19]

Wu et al.

[11] Patent Number: 6,066,770
[45] Date of Patent: May 23, 2000

[54] SELECTIVATED ZEOLITIC HYDROCARBON CONVERSION CATALYST

[75] Inventors: An-hsiang Wu, Bartlesville; Charles A. Drake, Nowata, both of Okla.

[73] Assignee: Phillips Petroleum Company, Bartlesville, Okla.

[21] Appl. No.: 09/186,984

[22] Filed: Nov. 5, 1998

[51] Int. Cl.[7] .................................................. C07C 5/22
[52] U.S. Cl. ............................ 585/475; 502/60; 502/63; 502/64; 502/71; 502/85
[58] Field of Search ............................... 585/475; 502/60, 502/63, 64, 71, 85

[56] References Cited

U.S. PATENT DOCUMENTS

| | | | |
|---|---|---|---|
| 4,090,981 | 5/1978 | Rodewald | 252/455 |
| 4,097,367 | 6/1978 | Haag et al. | 208/135 |
| 4,127,616 | 11/1978 | Rodewald | 260/671 |
| 4,283,306 | 8/1981 | Herkes | 252/432 |
| 4,465,886 | 8/1984 | Rodewald | 585/467 |
| 4,477,583 | 10/1984 | Rodewald | 502/71 |
| 4,950,835 | 8/1990 | Wang et al. | 585/467 |
| 5,476,823 | 12/1995 | Beck et al. | 502/60 |
| 5,495,059 | 2/1996 | Beck et al. | 585/470 |
| 5,516,736 | 5/1996 | Chang et al. | 502/64 |
| 5,574,199 | 11/1996 | Beck et al. | 585/407 |
| 5,602,066 | 2/1997 | Beck et al. | 502/64 |
| 5,675,047 | 10/1997 | Beck et al. | 585/467 |
| 5,800,696 | 9/1998 | Drake et al. | 208/135 |

*Primary Examiner*—Tom Dunn
*Attorney, Agent, or Firm*—Ryan N. Cross

[57] ABSTRACT

A catalyst, method for preparing the catalyst, and method for using the catalyst having improved para-selectivity in the conversion of alkyl-substituted benzene to para-dialkyl-substituted benzene. The catalyst being prepared by calcining a starting zeolite material, selectivating the calcined zeolite using a silicon-containing selectivating agent, physically mixing the calcined and selectivated zeolite with a binder, shaping the resulting zeolitic physical blend into a form suitable for use in a hydrocarbon conversion process, selectivating the shaped zeolitic physical blend using a silicon-containing selectivating agent, and calcining the selectivated shaped zeolitic physical blend.

29 Claims, No Drawings

SELECTIVATED ZEOLITIC HYDROCARBON CONVERSION CATALYST

FIELD OF THE INVENTION

This invention relates to a composition useful for converting an alkyl-substituted benzene to a para-dialkyl-substituted benzene, to a process for producing the composition, and to a process for using the composition to convert an alkyl-substituted benzene to a para-dialkyl-substituted benzene.

BACKGROUND OF THE INVENTION

It is well known to those skilled in the art that a representative para-dialkyl-substituted benzene is para-xylene. The production of para-xylene is typically performed by methylation or disproportionation of toluene over a catalyst under conversion conditions. Examples include the reaction of toluene with methanol as described in Chen et al., Journal of Amer. Chem. Soc., 101, 6783 (1979), and toluene disproportionation, as described by Pines in "The Chemistry of Catalytic Hydrocarbon Conversions", Academic Press, N.Y., 1981, p. 72. Such methods typically result in the production of a mixture including para-xylene, ortho-xylene, and meta-xylene. Depending on the degree of selectivity of the catalyst for para-xylene (para-selectivity) and the reaction conditions, different percentages of para-xylene are obtained. The yield, i.e., the amounts of xylene produced as a proportion of the feedstock, is also effected by the catalyst and the reaction conditions.

Economically, para-xylene is a more attractive product than ortho-xylene and meta-xylene. Unfortunately, the separation of para-xylene from ortho-xylene and meta-xylene is difficult and expensive. Accordingly, because of the large scale economics involved in the production processes, even a small improvement in the para-xylene selectivity of the process can add millions of dollars to the bottom line. Consequently, methods for increasing the para-selectivity of zeolite catalysts are of great importance.

SUMMARY OF THE INVENTION

An object of the invention is to provide an improved catalyst for converting an alkyl-substituted benzene to a dialkyl-substituted benzene, which catalyst has better selectivity for producing para-dialkyl-substituted benzene compared to prior catalysts. Another object of the invention is to provide a process for making such a catalyst. Also, an object of the invention is to provide a process for using the catalyst in the conversion of alkyl-substituted benzene to para-dialkyl-substituted benzene.

The invention includes a process for making a novel catalyst composition for use in converting hydrocarbons. This novel catalyst composition is made by calcining a zeolite prior to treating the catalyst with a selectivating agent, selectivating the calcined zeolite using a silicon-containing selectivating agent, physically mixing the calcined and selectivated zeolite with a binder, shaping the resulting zeolitic physical blend into a form suitable for use in a hydrocarbon conversion process, selectivating the shaped zeolitic physical blend using a silicon-containing selectivating agent, and calcining the resulting selectivated shaped zeolitic physical blend. The invention provides for the conversion of alkyl-substituted benzene to para-dialkyl-substituted benzene by contacting under conversion conditions a hydrocarbon feed with the inventive catalyst.

Other objects and advantages of the invention will become apparent from the detailed description and the appended claims.

DETAILED DESCRIPTION OF THE INVENTION

The inventive composition includes a zeolite starting material. The zeolite starting material used in the composition of the invention can be any zeolite which is effective in the conversion of alkyl-substituted benzene to para-dialkyl-substituted benzene when contacted under suitable reaction conditions with alkyl-substituted benzene. Preferably, the zeolite has a constraint index (as defined in U.S. Pat. No. 4,097,367, which is incorporated herein by reference) in the range of from about 0.4 to about 12, preferably from or about 2 to about 9. Generally, the molar ratio of $SiO_2$ to $Al_2O_3$ in the crystalline framework of the zeolite is at least about 5:1 and can range up to infinity. Preferably, the molar ratio of $SiO_2$ to $Al_2O_3$ in the zeolite framework is in the range from about 8:1 to about 200:1, more preferably from about 12:1 to about 100:1. Preferred zeolites include ZSM-5, ZSM-8, ZSM-11, ZSM-12, ZSM-35, ZSM-38, and mixtures thereof. The presently more preferred zeolites are ZSM-5 also known as "MFI".

In order to make the inventive composition, the starting zeolite material must first be calcined prior to treating the catalyst with a selectivating agent ("pre-calcine"). Pre-calcination can be performed by any suitable method known in the art, such as exposing the zeolite material to a gas atmosphere under temperature and pressure conditions for a period of time that suitably provides a calcined material. The gas used in the pre-calcination of the zeolite can be selected from the group consisting of inert gases (for example, nitrogen, helium, and argon gases), reducing gases (for example, carbon monoxide and hydrogen gases), air, oxygen, and steam, preferably the gas is selected from the group consisting of air, oxygen, nitrogen and mixtures of one or two thereof. The pre-calcining temperature is generally in the range from about 100° C. to about 1000° C., and preferably from about 500° C. to about 600° C. Generally, the pre-calcination may be conducted at a pressure from below atmospheric upwardly to about 1000 psia, preferably from about atmospheric to about 100 psia. The time period for exposing the zeolite starting material to the atmosphere at appropriate temperature conditions ranges from about 0.1 hour to about 30 hours, preferably from about 0.5 hour to about 10 hours.

The pre-calcined zeolite is then selectivated by depositing a silicon-containing selectivating agent on the pre-calcined zeolite using any suitable method known in the art. The silicon-containing selectivating agent may be in the form of a solution, an emulsion, a liquid or a gas under the conditions of contact with the pre-calcined zeolite. Examples of methods of depositing silicone on a zeolite are found in U.S. Pat. Nos. 4,090,981, 4,127,616, 4,465,886 and 4,477,583 to Rodewald, which are incorporated by reference herein. Further examples of silicone deposition on zeolite surfaces are described in U.S. Pat. No. 4,950,835 to Wang et al. A preferred method of depositing the silicon-containing selectivating agent on the pre-calcined zeolite is to soak the pre-calcined zeolite in a selectivating solution containing a selectivating agent dissolved in a carrier, then allowing the system to dry by evaporation.

The silicon-containing compound of the selectivating agent may comprise organosilicon compounds and is preferably a silicone, a silane or a mixture thereof. Examples of silicones which are useful as selectivating agents are organic silicone compounds such as phenyl methyl silicone, dimethyl silicone, and blends thereof. If a silane is chosen as a selectivating agent, the more preferred silanes are alkoxy silanes or organoamine silanes. It is preferred that the silicon-containing compound will dissolve or at least emulsify in the carrier, as well as take advantage of the hydrophobic character of the zeolite on which the silicon-containing compounds are being deposited. The presently preferred silicon-containing compounds are tetraalkyl orthosilicates and mixtures thereof. Presently, the most preferred silicon-containing compound is tetraethyl orthosilicate.

The carrier within which the selectivating agent is dissolved may be any suitable liquid carrier, more preferably the carrier should be an organic substance and most preferably the carrier is a nonpolar or aprotic organic solvent, such as cyclohexane. The pre-selectivating solution containing a selectivating agent and a carrier may contain a selectivating agent in an amount which is greater than about 1 weight percent and less than about 99 weight percent, more preferably greater than about 2 weight percent and less than about 50 weight percent, even more preferably greater than about 5 weight percent and less than about 20 weight percent, and most preferably about 10 weight percent of the selectivating solution.

Following deposition of the silicon-containing selectivating agent on the pre-calcined zeolite, the selectivation step is completed by calcining the modified pre-calcined zeolite to remove any remaining carrier and to convert any liquid silicon compound to a solid residue material thereof. Calcination can be performed by any suitable method known in the art and, generally, will be carried out in accordance with the conditions outlined previously for the pre-calcine step.

Following the calcination and selectivation steps above, the modified zeolite is physically mixed with a binder to produce a zeolitic physical blend of modified zeolite and binder. Any binders known to one skilled in the art for use with a zeolite are suitable for use herein. Examples of suitable binders include, but are not limited to, aluminas, such as, for example, alpha-alumina and gamma-alumina; silicas; alumina-silica; aluminum phosphate; aluminum chlorohydrate; clays, such as kaolinite, halloysite, vermiculite, attapulgite, montmorillonite, and combinations of any two or more thereof. The presently preferred binder is an inorganic binder containing silica, preferably between 20% and 60% by weight of $SiO_2$, and more preferably between 30% and 50% by weight of $SiO_2$. The amount of binder to be mixed with the modified zeolite can be of a quantity of from about 10 weight percent to about 1000 weight percent, more preferably from about 50 weight percent to about 200 weight percent, and most preferably from about 80 weight percent to about 120 weight percent of the modified zeolite. The modified zeolite and binder can be physically mixed at about 15° C. to about 100° C. under atmospheric pressure, or any other pressure, generally, with liquids, such as water or hydrocarbons, by any means known to one skilled in the art, such as stirring, blending, or kneading.

The zeolitic physical blend is then shaped into a form suitable for use in a hydrocarbon conversion process. Shaping of the zeolitic physical blend can be performed by extrusion, pelletizing, tableting, or any other suitable means. The resulting shaped zeolitic physical blend comprises individual pieces with surface areas generally ranging from about 50 $m^2/g$ to about 700 $m^2/g$.

The shaped zeolitic physical blend is then calcined. Calcination of the shaped zeolitic physical blend can be performed by any suitable method known in the art but, generally, will be in accordance with the conditions outlined above for the pre-calcine step.

The shaped zeolitic physical blend is then selectivated a second time by depositing a silicon-containing selectivating agent on the shaped zeolitic physical blend using any suitable method. The silicon-containing selectivating agent may be in the form of a solution, an emulsion, a liquid or a gas under the conditions of contact with the shaped zeolitic physical blend. A preferred method of depositing the selectivating agent on the shaped zeolitic physical blend is impregnation by the incipient wetness method. Using conventional incipient wetness techniques, a determination may be made as to the amount of carrier required to saturate and fill the pores of the shaped zeolitic physical blend. A selectivating solution may then be prepared utilizing the predetermined amount of carrier and a sufficient amount of selectivation agent. The selectivating solution may then be incrementally added to the shaped zeolitic physical blend until its outer surface appears saturated, where upon addition of the selectivating solution is halted.

The silicon-containing selectivating agent and the carrier should be in accordance with the description provided previously.

Following deposition of the silicon-containing selectivating agent on the shaped zeolitic physical blend, the selectivation step is completed by calcining the modified zeolitic physical blend to remove any remaining carrier and to convert any liquid silicon compound to a solid residue material thereof. Calcination can be performed by any suitable method known in the art, but generally will be carried out in accordance with the conditions outlined for the pre-calcine step.

Zeolites modified in accordance with the present invention are generally useful as catalysts in shape selective hydrocarbon conversion processes, particularly shape selective disproportionation of alkyl-substituted benzenes to yield dialkyl-substituted benzenes. The catalyst of the present invention is advantageously used in the conversion of alkyl benzene compounds to provide dialkyl-substituted benzene products which are highly enriched in the para-dialkyl-substituted benzene isomer. Conversion reactions of this type include aromatics alkylation, transalkylation and disproportionation of aromatics.

The modified catalysts of the present invention have been found to be particularly useful in the selective production of para-dialkyl-substituted benzenes containing alkyl groups of 1 to 4 carbon atoms, such as para-xylene. Such processes are typified by the disproportionation, in the presence of the modified catalyst, of a hydrocarbon precursor, typically a monoalkyl-substituted benzene having 1 to 4 carbon atoms in the alkyl substituent.

In general, such disproportionation is carried out under catalytic conversion conditions over a catalyst comprising the modified zeolite. The catalytic conversion conditions typically comprise a temperature of from about 100° C. to about 760° C., a pressure of from about 0.1 atmosphere (bar) to about 5000 atmospheres (bar), a weight hourly space velocity (WHSV) of from about 0.08 $hr^{-1}$ to about 2000 $hr^{-1}$, and a hydrogen/organic, e.g., hydrocarbon compound (HC), mole ratio of from 0 to about 100.

More specifically, the present invention is described in detail below in relation to the disproportionation of alkyl-substituted benzenes, particularly toluene, over the inventive catalyst. Normally, a single pass conversion of an alkyl benzene stream results in a product stream which includes dialkyl benzenes having alkyl groups at each possible combination of two locations, i.e., o-, m-, and p-dialkyl benzenes. A catalyst treated in the manner described herein yields a significantly para-selected product from alkyl benzene disproportionation.

The invention also comprises the selective conversion of alkyl benzene to para-dialkyl benzene by disproportionating alkyl benzene in a reaction stream containing an alkyl benzene feed with the inventive catalyst, optionally in the presence of hydrogen, and at reaction conditions suitable to provide p-dialkyl benzene selectivity of greater than about 85%, preferably greater than 95%. The product stream may also contain small amounts of o- and m-dialkyl benzene and trace amounts of impurities.

As used herein, the term "para-dialkyl benzene selectivity" means the proportion of p-dialkyl benzene, indicated as a percentage, among the dialkyl benzene products, i.e., p-dialkyl benzene, o-dialkyl benzene, and m-dialkyl benzene. Those skilled in the art will appreciate that the relative proximity of the boiling points of these isomers necessitates relatively expensive separation processes for the isolation of p-dialkyl benzene. On the other hand, p-dialkyl benzenes are more readily separated from other components in the product stream such as benzene, monoalkyl benzenes and other alkyl-substituted benzenes. Furthermore, the dialkyl benzenes are known to proceed in reactions which produce unwanted heavier alkyl benzenes.

The present invention provides a process for obtaining p-dialkyl benzenes at alkyl benzene conversion rates of at least 20%, preferably at least about 25% to about 30%, with a p-dialkyl benzene selectivity of greater than 85%, generally, greater than 90% and preferably at least 95%.

The alkyl benzene feedstock preferably includes about 75% to 100% alkyl benzene, more preferably at least about 95% alkyl benzene. Other compounds such as benzene and other alkyl-substituted benzenes may also be present in the alkyl benzene feedstock without adversely affecting the present invention.

The alkyl benzene feedstock may also be dried, if desired, in a manner which will minimize moisture entering the reaction zone. Numerous methods known in the art are suitable for drying the alkyl benzene charge for the process of the invention. These methods include percolation through any suitable desiccant, for example, silica gel, activated alumina, molecular sieves or other suitable substances, or the use of liquid charge dryers.

The catalyst of the present invention is contacted with the alkyl benzene feedstock under conditions for effecting vapor-phase disproportionation. Conditions effective for accomplishing the high para-selectivity and acceptable alkyl benzene disproportionation conversion rates include a reactor inlet temperature of from about 200° C. to about 600° C., preferably from about 350° C. to about 500° C.; a pressure of from about atmospheric to about 5000 psig, preferably from about 100 to about 1000 psig; a WHSV of from about 0.1 hr$^{-1}$ to about 20 hr$^{-1}$, preferably from about 2 hr$^{-1}$ to about 10 hr$^{-1}$; and a H$_2$/HC mole ratio of from about 0.05 to about 20, preferably from about 0.1 to about 6. This process may be conducted in either batch or fluid bed operation, with the attendant benefits of either operation readily obtainable. The effluent may be separated and distilled to remove the desired product, i.e., the para isomer, as well as other by-products. Alternatively, the appropriate fraction may be subjected to further separation, in the case of xylenes, subjected to crystallization to yield p-xylene.

EXAMPLES

The following examples more clearly illustrate the catalyst of the present invention and comparable catalysts. Each catalyst was tested for its effectiveness in the disproportionation of toluene into para-xylene by contacting the catalyst with at least 95% pure toluene in a disproportionation process as described above, under the following conditions:

Temperature: 780° F.–820° F.

Pressure: 495 psig–505 psig

Carrier: Hydrogen

Carrier Feed Rate: 0.30 Cubic Feet per Hour (CFH)

Toluene Feed Rate: 35.0 mL/hr–45.0 mL/hr

Weight Hourly Space Velocity (WHSV): 2.0 hr$^{-1}$–5.0 hr$^{-1}$

Test results were evaluated in terms of weight percent of toluene converted, the ratio para-xylene to total xylenes produced, toluene disproportionation index and the weight percent of para-xylene produced. Table 1 provides a summary of test results for the catalysts whose preparations are illustrated by the following examples.

Example 1

A catalyst in accordance with the present invention was prepared by modifying the commercially available MFI zeolite (provided by Universal Oil Products, Des Plaines, Ill.) as follows.

A 33 gram sample of MFI zeolite powder was calcined in air at 538° C. for 2 hours. The pre-calcined zeolite was then placed in an evaporator dish and pre-selectivated by adding 66 grams of a pre-selectivating solution, having as its constituents 6.6 grams of tetraethyl orthosilicate dissolved in 59.4 grams of cyclohexane, without stirring. The resulting combination of pre-calcined zeolite and selectivating solution was then allowed to dry by evaporation in dry argon at room temperature for 16 hours, and was thereafter calcined in air at 538° C. for 6 hours.

The resulting zeolite was then physically mixed with 33 grams of a commercially available silica colloidal binder sold as Ludox AS-40 binder (provided by DuPont, Wilmington, Del.). The physical blend of zeolite and binder was then extruded into ¹⁄₁₆" extrudate and calcined in air at a temperature of 538° C. for 6 hours.

18.24 grams of the resulting dried extrudate was then selectivated by contacting its outer surface with 6.67 grams of a selectivating solution, having as its constituents 0.67 grams of tetraethyl orthosilicate dissolved in 6.0 grams of a cyclohexane, using the incipient wetness method. The wetted extrudate was then calcined in air at 538° C. for 6 hours.

The resulting catalyst was designated Catalyst 1.

Example 2

A second catalyst was prepared using methods similar to those of Catalyst 1; however, the preparation did not include a second selectivation step.

A 33 gram sample of MFI zeolite powder was calcined in air at 538° C. for 2 hours. The pre-calcined zeolite was then placed in an evaporator dish and selectivated by adding 66 grams of a selectivating solution, having as its constituents 6.6 grams of tetraethyl orthosilicate dissolved in 59.4 grams of cyclohexane, without stirring. The resulting combination of pre-calcined zeolite and selectivating solution was then allowed to dry by evaporation in air at room temperature for 16 hours, and was thereafter calcined in argon at 538° C. for 6 hours.

The resulting zeolite was then physically mixed with 33 grams of commercially available Ludox AS-40 binder. The physical blend of zeolite and binder was then extruded into ¹⁄₁₆" extrudate and calcined in air at a temperature of 538° C. for 6 hours.

The resulting catalyst was designated Catalyst 2.

Example 3

A third catalyst was prepared using methods similar to those of Catalyst 1; however, the preparation did not include a second selectivation step and the selectivation solution used ethanol as a solvent rather than cyclohexane.

A 10 gram sample of MFI zeolite powder was calcined in air at 538° C. for 2 hours. The pre-calcined zeolite was then placed in an evaporator dish and selectivated by adding 20 grams of a selectivating solution, having as its constituents 2.0 grams of tetraethyl orthosilicate dissolved in 18.0 grams of ethanol, without stirring. The resulting combination of pre-calcined zeolite and selectivating solution was then allowed to dry by evaporation in air at room temperature for 16 hours, and was thereafter calcined in air at 538° C. for 6 hours.

The resulting zeolite was then physically mixed with 10 grams of commercially available Ludox AS-40 binder. The physical blend of zeolite and binder was then extruded into 1/16" extrudate and calcined in air at a temperature of 538° C. for 6 hours.

The resulting catalyst was designated Catalyst 3.

Example 4

A fourth catalyst was prepared using methods similar to those of Catalyst 1; however, the preparation did not include a pre-calcination step or a second selectivation step.

A 10 gram sample of MFI zeolite powder was placed in an evaporator dish and pre-selectivated by adding 20 grams of a selectivating solution, having as its constituents 2.0 grams of tetraethyl orthosilicate dissolved in 18.0 grams of cyclohexane, without stirring. The resulting combination of zeolite and selectivating solution was then allowed to dry by evaporation in argon at room temperature for 16 hours, and was thereafter calcined in air at 538° C. for 6 hours.

The resulting zeolite was then physically mixed with 10 grams of commercially available Ludox AS-40 binder. The physical blend of zeolite and binder was then extruded into 1/16" extrudate and calcined in air at a temperature of 538° C. for 6 hours.

The resulting catalyst was designated Catalyst 4.

Example 5

A fifth catalyst was prepared using methods similar to those of Catalyst 1; however, the preparation did not include a pre-calcination step or a first selectivation step.

A 10 gram sample of MFI zeolite powder was physically mixed with 10 grams of commercially available Ludox AS-40 binder. The physical blend of zeolite and binder was then extruded into 1/16" extrudate and calcined in air at a temperature of 538° C. for 6 hours.

The resulting dried extrudate was then selectivated by contacting its outer surface with 20 grams of a selectivating solution, having as its constituents 2.0 grams of tetraethyl orthosilicate dissolved in 18.0 grams of cyclohexane, using the incipient wetness method. The wetted extrudate was then calcined in air at 538° C. for 6 hours.

The resulting catalyst was designated Catalyst 5.

Example 6

A sixth catalyst was prepared using methods similar to those of Catalyst 1; however, the preparation did not include a pre-calcination step, a first selectivation step, or a second selectivation step.

A 20 gram sample of MFI zeolite powder was physically mixed with 20 grams of commercially available Ludox AS-40 binder. The physical blend of zeolite and binder was then extruded into 1/16" extrudate and calcined in air at 538° C. for 6 hours.

The resulting catalyst was designated Catalyst 6.

TABLE 1

| Catalyst Number | Pre-Calcination | First Selectivation | Second Selectivation | Final Calcination | Wt-% Tol Conv. | % p-Xyl/ΣXyln | TDP Index* | Wt-% p-Xyln |
|---|---|---|---|---|---|---|---|---|
| 1 | 538° C./2 hrs. | TEOS/cy-C6 | TEOS/cy-C6 | 538° C./6 hrs. | 27.5 | 100.0 | 27.5 | 12.2 |
| 2 | 538° C./2 hrs. | TEOS/cy-C6 | — | 538° C./6 hrs. | 34.6 | 61.7 | 21.3 | 10.4 |
| 3 | 538° C./2 hrs. | TEOS/EtOH | — | 538° C./6 hrs. | 36.6 | 23.9 | 8.7 | 4.1 |
| 4 | — | TEOS/cy-C6 | — | 538° C./6 hrs. | 36.9 | 24.5 | 9.0 | 4.3 |
| 5 | — | — | TEOS/cy-C6 | 538° C./6 hrs. | 36.0 | 23.4 | 8.4 | 4.0 |
| 6 | — | — | — | 538° C./6 hrs. | 42.0 | 22.6 | 9.5 | 5.3 |

$$^*\text{Toluene Disproportionation Index} = \frac{(\text{Wt-\% Tol Conv.})(\text{\% p-Xyl}/\Sigma\text{Xyln})}{100}$$

Catalyst 1 is a preferred embodiment of the present invention. As illustrated in Table 1, Catalyst 1 is far more para-xylene selective than Catalysts 2–6. Catalyst 1 produces xylene products from toluene disproportionation which are 100% para-xylene, whereas Catalysts 2–6 produce xylene products from toluene disproportionation which range from 22.6% to 61.7% para-xylene. The high para-selectivity demonstrated by Catalyst 1 allows for a toluene disproportionation process which yields 12.2 weight percent of para-xylene. This yield is superior to that of Catalysts 2–6 which allow for a toluene disproportionation process which yields between 5.3 and 10.4 weight percent of para-xylene. In addition to providing higher yields of para-xylene, the high para-selectivity demonstrated by Catalyst 1 allows for toluene disproportionation processes which produces less undesirable products and, hence, is more economically efficient.

Obviously, many modifications and variations of the present invention are possible in light of the above teachings. It is, therefore, to be understood that within the scope of the appended claims, the invention may be practiced otherwise than as specifically described.

That which is claimed is:

1. A catalyst comprising:
   a physical blend of a zeolite and a binder, said zeolite having been calcined and thereafter selectivated with a silicon-containing selectivating agent to produce a modified zeolite, said modified zeolite being physically mixed with said binder, and said physical blend of said modified zeolite and said binder having been selectivated with a silicon-containing selectivating agent and thereafter calcined subsequent to the physical mixing of said zeolite and said binder.

2. A catalyst in accordance with claim 1 wherein said selectivating agent is an organosilicon compound or a mixture of organosilicon compounds.

3. A catalyst in accordance with claim 2 wherein said selectivating is with a selectivating solution containing said selectivating agent dissolved in an organic solvent.

4. A catalyst in accordance with claim 3 wherein said organic solvent is an aprotic organic solvent and said binder is an inorganic binder containing silica.

5. A catalyst in accordance with claim 4 wherein said aprotic organic solvent is cyclohexane.

6. A catalyst in accordance with claim 5 wherein said selectivating solution contains said selectivating agent in an amount between about 5% and about 20% by weight.

7. A catalyst in accordance with claim 6 wherein said selectivating agent is selected from silicones, silanes and mixtures thereof.

8. A catalyst in accordance with claim 7 wherein said selectivating agent is a tetraalkyl orthosilicate or mixtures thereof.

9. A catalyst in accordance with claim 3 wherein said selectivating is with a selectivating solution containing tetraalkyl orthosilicate dissolved in an organic solvent.

10. A catalyst in accordance with claim 9 wherein said organic solvent is an aprotic organic solvent and said binder is an inorganic binder containing silica.

11. A catalyst in accordance with claim 10 wherein said aprotic organic solvent is cyclohexane.

12. A catalyst in accordance with claim 11 wherein said selectivating solution contains said selectivating agent in an amount between about 5% and about 20% by weight.

13. A process for preparing a catalyst which comprises:
    (a) calcinating a zeolite;
    (b) selectivating said calcined zeolite using a silicon-containing selectivating agent;
    (c) calcining said calcined selectivated zeolite to produce a modified zeolite;
    (d) mixing said modified zeolite with a binder to produce a physical blend;
    (e) selectivating said physical blend using a selectivating agent; and
    (f) calcining the resulting selectivated physical blend.

14. A process for preparing a catalyst in accordance with claim 13 wherein said selectivating agent is selected from organosilicon compounds and mixtures thereof.

15. A process for preparing a catalyst in accordance with claim 14 which further comprises:
    dissolving said selectivating agent in a carrier prior to producing a selectivating solution.

16. A process for preparing a catalyst in accordance with claim 15 wherein said carrier is an aprotic organic solvent.

17. A process for preparing a catalyst in accordance with claim 16 wherein said selectivating solution contains said selectivating agent in an amount between about 2% and about 50% by weight.

18. A process for preparing a catalyst in accordance with claim 17 wherein said aprotic organic solvent is cyclohexane.

19. A process in accordance with claim 18 wherein said selectivating agent is selected from silicones, silanes and mixtures thereof.

20. A process for preparing a catalyst in accordance with claim 19 wherein said selectivating agent is selected from tetraalkyl orthosilicates and mixtures thereof.

21. A process for hydrocarbon conversion comprising contacting a hydrocarbon feed with a catalyst under conditions effective to convert said hydrocarbon feed to a hydrocarbon product different from said hydrocarbon feed, the improvement comprises using as said catalyst a physical blend of a zeolite and a binder, said zeolite having been calcined and thereafter selectivated with a silicon-containing selectivating agent prior to being physically mixed with said binder, and said physical blend of said zeolite and said binder having been selectivated with a silicon-containing selectivating agent and thereafter calcined.

22. A process for hydrocarbon conversion in accordance with claim 21 wherein said selectivating agent is selected from organosilicon compounds and mixtures thereof.

23. A process for hydrocarbon conversion in accordance with claim 22 wherein said selectivating is with a selectivating solution containing said selectivating agent dissolved in an organic solvent.

24. A process for hydrocarbon conversion in accordance with claim 23 wherein said organic solvent is an aprotic organic solvent and said binder is an inorganic binder containing silica.

25. A process for hydrocarbon conversion in accordance with claim 24 wherein said aprotic organic solvent is cyclohexane.

26. A process for hydrocarbon conversion in accordance with claim 25 wherein said selectivating solution contains said selectivating agent in an amount between about 5% and about 20% by weight.

27. A process in accordance with claim 26 wherein said selectivating agent is selected from silicones, silanes and mixtures thereof.

28. A process for hydrocarbon conversion in accordance with claim 27 wherein said selectivating agent is selected from tetraalkyl orthosilicates and mixtures thereof.

29. A process in accordance with claim 28 wherein said hydrocarbon feed comprises toluene, said hydrocarbon product comprises para-xylene and said conversion is by disproportionation.

* * * * *